United States Patent [19]

Kinsman

[11] Patent Number: 5,359,999
[45] Date of Patent: Nov. 1, 1994

[54] ASYNCHRONOUS CYCLING OF MECHANICAL VENTILATORS

[76] Inventor: James B. Kinsman, 177 Heather La., Macedon, N.Y. 14502

[21] Appl. No.: 23,131

[22] Filed: Feb. 24, 1993

Related U.S. Application Data

[63] Continuation of Ser. No. 718,263, Jun. 20, 1991, abandoned.

[51] Int. Cl.$^5$ ............................................. A61M 16/00
[52] U.S. Cl. ............................ 128/204.21; 128/204.23; 601/9
[58] Field of Search ............... 128/28, 30.2, 207.14, 128/207.15, 204.21, 204.23

[56] References Cited

U.S. PATENT DOCUMENTS

| | | | |
|---|---|---|---|
| 2,699,163 | 1/1955 | Engström | 601/44 |
| 3,566,862 | 3/1971 | Schuh et al. | 128/30.2 |
| 3,683,655 | 8/1972 | White et al. | 128/30.2 |
| 4,248,221 | 2/1981 | Winnard | 128/207.15 |
| 4,328,799 | 5/1982 | Lo Piano | 128/202.12 |
| 4,397,306 | 8/1983 | Weisfeldt et al. | 128/28 |
| 4,453,545 | 6/1984 | Inoue | 128/207.15 |
| 4,474,571 | 10/1984 | Lasley | 128/202.12 |
| 4,621,621 | 11/1986 | Marsalis | 128/205.26 |
| 4,815,452 | 3/1989 | Hayek | 128/205.26 |
| 4,819,664 | 4/1989 | Nazari | 128/207.15 |
| 4,840,172 | 6/1989 | Augustine et al. | 128/207.14 |
| 4,881,527 | 11/1989 | Lerman | 128/28 |
| 4,928,674 | 5/1990 | Halperin et al. | 128/30.2 |
| 5,040,532 | 8/1991 | Alfery | 128/207.15 |

Primary Examiner—Edgar S. Burr
Assistant Examiner—Aaron J. Lewis
Attorney, Agent, or Firm—Susan J. Timian

[57] ABSTRACT

A system is disclosed for the use of two mechanical ventilators, wherein one of the ventilators is used to ventilate both lungs of a patient and the second ventilator is used to inflate a pneumobelt or similar device. Both ventilators are controlled to asynchronously cycle off and on at different times. Alternatively, the first and second ventilators are used to ventilate the first and second lung, respectively, of a patient using a double-lumen endotracheal tube, with both ventilators being controlled to asynchronously cycle off and on at different times.

12 Claims, 8 Drawing Sheets

ASYNCHRONOUS CYCLING OF MECHANICAL VENTILATORS

This application is a continuation of application Ser. No. 718,263, filed Jun. 20, 1991, now abandoned.

BACKGROUND OF THE INVENTION

Mechanical ventilator apparatus and related hardware have long been used in the medical profession for assisting or controlling pulmonary ventilation in situations where the patient requires endotracheal intubation. Intubation is indicated in patients who are unable to spontaneously maintain adequate arterial blood gas values secondary to inadequate respiratory pattern or volumes. This deficit is attributable to a neurological, pulmonary and/or cardiovascular insult, injury or disease process. For example, U.S. Pat. Nos. 3,683,655; 4,397,306; and 4,815,452 illustrate various systems and apparatus used to control and/or assist ventilation. In addition, the assistance of an increase in blood flow from the liver to the heart is required for the purpose of post-operatively maintaining or attempting to obtain better patient blood pressure following some post-operative cardiac procedures. In the Fontan Procedure, in which the patient has no functional right atrium or right ventricle, another goal is to overcome the increased pulmonary vascular resistance to systemic blood flow which in turn, increases oxygenation. In application, various devices such as inflatable bladders and assemblies are sometimes wrapped around the abdominal area. These sometimes are referred to as "pneumobelts". The above-mentioned U.S. Pat. Nos. 3,683,655 and 4,397,306 also illustrate the use of inflatable devices of this type.

A common problem associated with the combined use of two ventilators to simultaneously drive the device described above and to ventilate the patient via an endotracheal tube is that the cycling of these devices is not properly coordinated to provide for maximum efficiency and maximum blood return to the heart and thoracic vessels.

The particular object of the present invention is to utilize the liver's blood reservoir-like properties as a voluminous source to provide additional thoracic blood return which will assist in maintaining an adequate blood pressure and pulmonary circulation in the patient. It is, therefore, an object of the present invention to overcome the disadvantages associated with the prior art referred to above.

Another object of the present invention is to provide an improved system and method wherein the combination of two ventilators used in conjunction with an endotracheal tube and pneumobelt are coordinated so that they work efficiently in tandem in order to obtain improved results in the arterial blood gas values, and maximum possible blood return to the thoracic cavity.

SUMMARY OF THE INVENTION

The present invention is directed to ventilating both lungs of a patient using conventional mechanical ventilation techniques through a standard endotracheal tube, while at the same time using a second ventilator to intermittently inflate and pressurize an air bladder or pneumobelt. The objective of the pneumobelt, which is wrapped tightly around the upper abdominal area of the patient, is to pressurize the liver to cause an increased blood flow from the liver to the heart which aids in overcoming the pulmonary vascular resistance and thus improving oxygenation. The pneumobelt assembly usually consists of an air bladder contained within materials such as canvas and velcro. The two ventilators are connected by a cable which is designed to provide for asynchronous cycling of the ventilators whereby they cycle off and on at different times in order to pressurize the pneumo belt and, therefore, encourage blood flow from the liver to the thorax alternating with the pressurization of the lungs for patient ventilation via a standard endotracheal tube connected to the second ventilator. Through the use of this system:

1) the blood flow from the liver to the thorax can be rapidly interspersed between the relatively high intrathoracic pressures caused by the mechanical ventilation of the patient,
2) a means is provided which allows for control of the coordination of the cycling off and on of the two ventilators,
3) increased thoracic blood return results in improved oxygenation (measured, arterial $PO_2$ levels) as the pulmonary vascular resistance is overcome thus allowing greater pulmonary circulation, and
4) post-operative patients, including but not limited to pediatric and adolescent cardiac surgery cases who have undergone the Fontan Procedure, can be expected to overcome life-threatening hypoxemia and hypotension more rapidly, thereby decreasing mortality rate and the duration of the patient's critical condition.

In a further embodiment of the present invention, the asynchronous cycling of ventilators can also be utilized for alternating lung ventilation, whereby each lung is ventilated individually via a double-lumen endotracheal tube similar to that used for synchronized independent lung ventilation. Through the use of this system on the most critical of patients, alternating lung ventilation provides for ventilating one lung at a time, rapidly alternating, resulting in decreased intrathoracic pressure at the point of peak inspiration in the respiratory cycle.

DETAILED DESCRIPTION OF THE INVENTION

Figure 1:
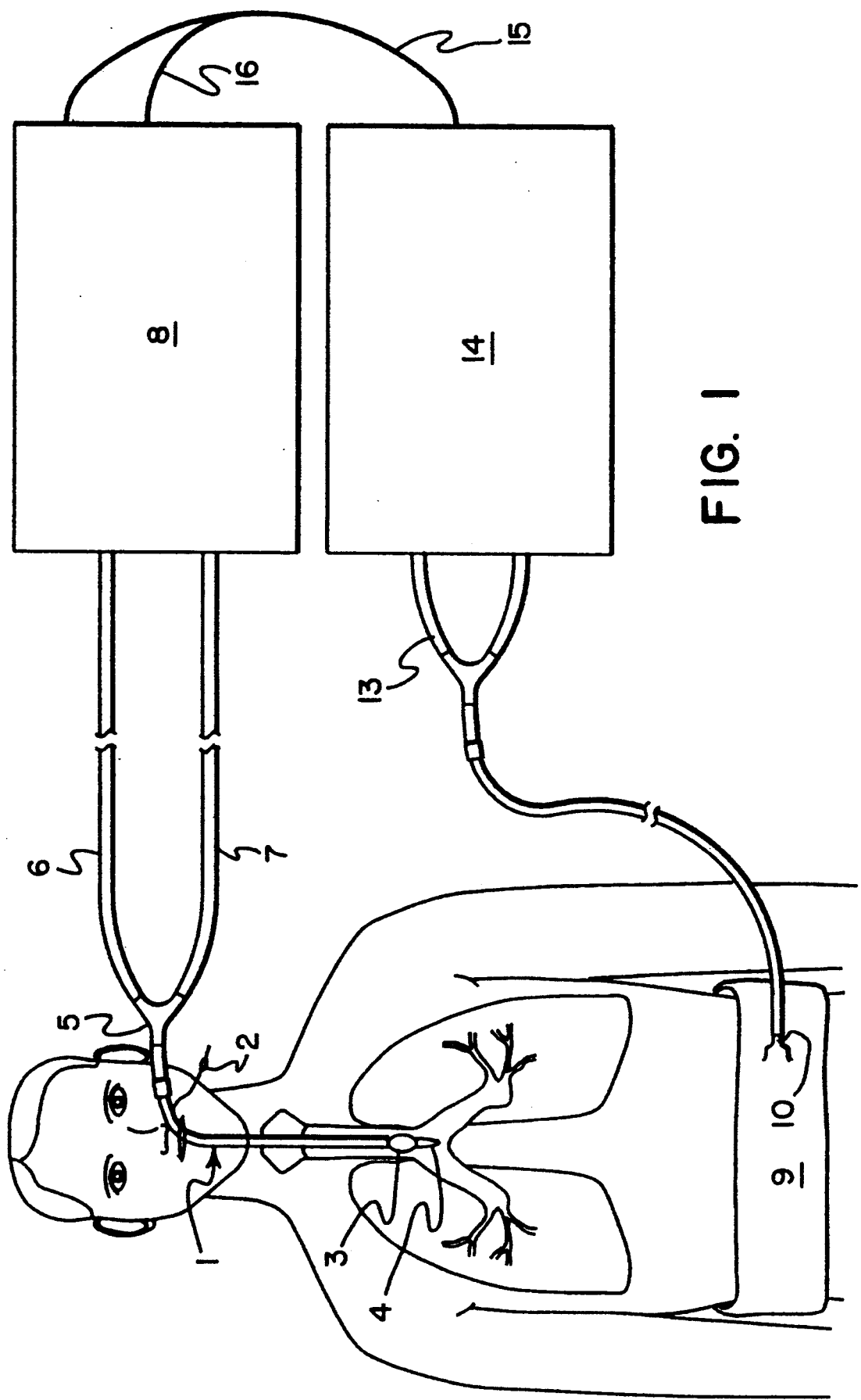
FIG. 1 is a schematic illustration of the present invention in which two ventilators are used to asynchronously cycle to ventilate a patient via an endotracheal tube and to pressurize a pneumo belt on a patient.

According to the present invention, as illustrated in FIG. 1, a patient is shown connected to Ventilator A via an endotracheal tube, with Ventill, tot B connected to a pneumobelt to provide alternating abdominal pressurization.

The patient is intubated with a standard, commercially available endotracheal tube 1 in place. The pilot balloon 2 is used as a syringe port to inflate and deflate the tube's cuff 3, which maintains an air seal against the tracheal wall so that all air passes in and out of the lungs instead of leaking around the endotracheal tube. In the case of neonatal patients, and in some pediatric patients, an uncuffed endotracheal tube is used. The orifice 4 at the tube's end allows for gas exchange between the mechanical ventilator 8 and the lungs. The ventilator circuit consisting of inspiratory and expiratory limbs 6 and 7 connects to a wye 5 which is connected to the endotracheal tube. A pneumobelt 9 is wrapped around the upper abdominal area of the patient and is connected to a second mechanical ventilator 14 via a connecting port 10 which can be 15 or 22 mm O.D. The inspiratory and expiratory limbs 13 of the ventilator circuit can be wyed together at the ventilator, since Ventilator B's only function is to pressurize the pneumo belt. Therefore, deadspace volume is not a factor. In the present invention, electrical cable 15 is designed to provide asynchronous cycling of two mechanical ventilators and is shown connecting the ventilators. For an explanation of the branching wire 16, see FIG. 4. For an expanded view of the standard endotracheal tube, see FIG. 6.

Figure 2:
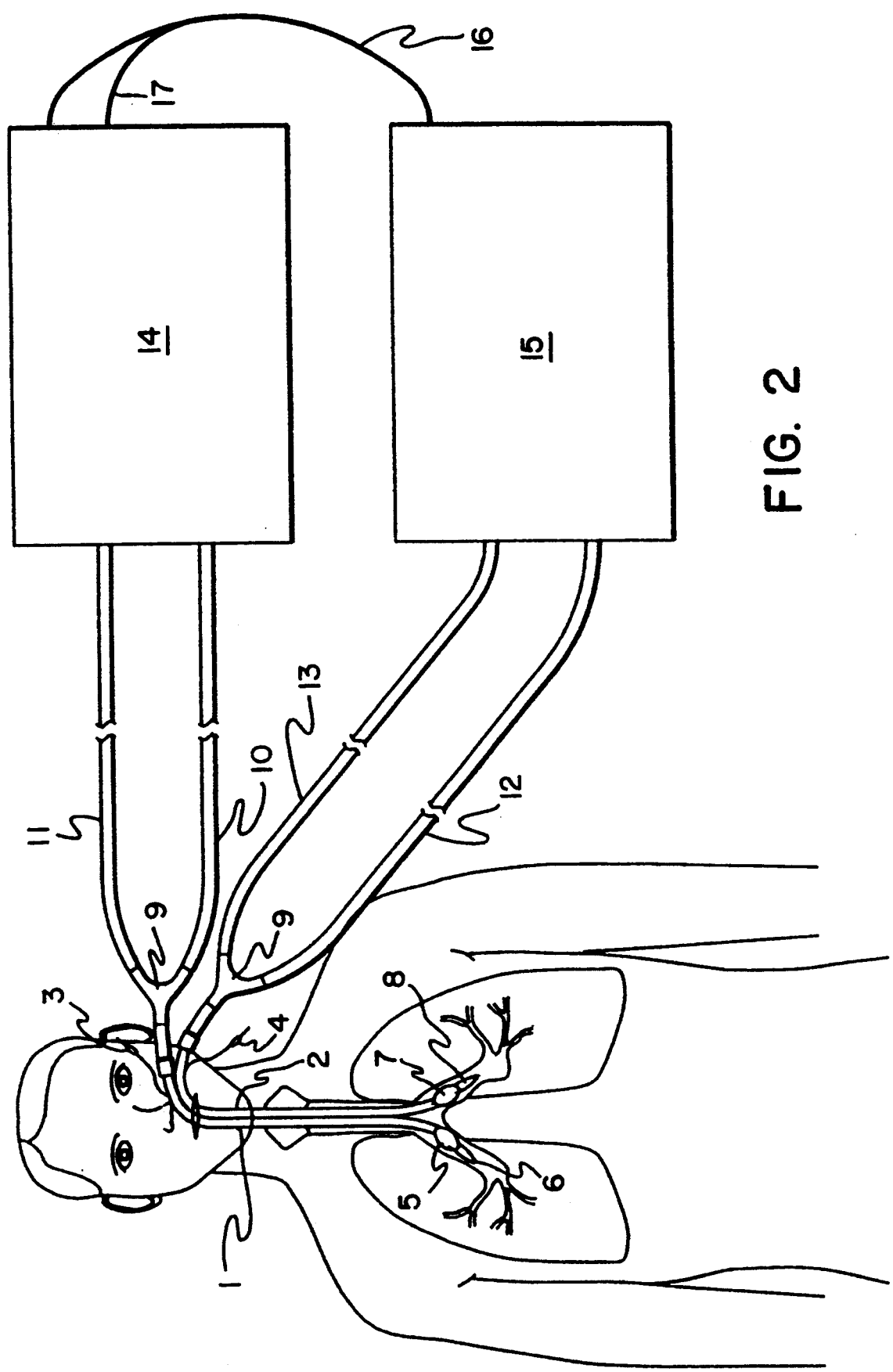
FIG. 2 is a schematic illustration of two ventilators being used on a patient to provide for alternating lung ventilation.

In another embodiment of the present invention, FIG. 2 illustrates a further use of two ventilators using an electrical cable designed to provide asynchronous cycling. This embodiment is similar to the set-up of FIG. 1, except FIG. 2 shows "Alternating Lung Ventilation" via a commercially available double-lumen endotracheal tube, and the pneumobelt is not in use.

The right and left lumens 1 and 2 comprise the commercially available double lumen endotracheal tube, and ventilate the right and left lungs, respectively. The pilot balloon 3 on the right lumen allows for inflation and deflation of the bronchus cuff 5 which provides an air seal for isolating the right lung at the level of the right mainstem bronchus, and acts as the distal seal for isolating the left lung. The lumen's orifice 6 at the end of the tube allows gas exchange to occur only in the right lung as long as the cuff's 5 seal is maintained. The left pilot balloon 4 allows for inflation and deflation of the left lumen's cuff 7 which lies against the tracheal wall and provides a proximal seal for the left lung. The lumen's orifice 8 is the left lung's gas exchange port. The ventilator circuits maintain separate closed systems for each ventilator 14 and 15 to its respective lung. The patient wyes, flex-tube and swivel adapter assemblies 9 connect the individual endotracheal tube lumens to the inspiratory limbs 10 and 12 and expiratory limbs 11 and 13. The cable 16/17 electrically connects Ventilator A and B and provides the means to alternate the cycling of the two ventilators, thus alternating the ventilation of the right and left lungs. For an expanded view and detailed description of the connecting cable, see FIGS. 4 and 8. The clinical practitioner has the option to utilize different ventilator parameters for each machine, such as mode, tidal volume, inspiratory pressure, PEEP (positive end expiratory pressure), $F_iO_2$ levels (fractional concentration of inspired oxygen), sensitivity, and/or alarm settings. In the case of the Siemens 900 C ventilator, the rate which is set on the Master ventilator is valid for the Slave ventilator also. Thus, regardless of its setting, the rate setting on the Slave is overridden. A beneficial clinical application of Alternating Lung Ventilation is in the severely hypotensive patient whose circulatory status (blood pressure and cardiac output) is compromised by peak inspiratory pressure and/or PEEP levels that occur or are used with conventional lung ventilation. For an expanded view of the double lumen endotracheal tube, see FIG. 7.

Figure 3:
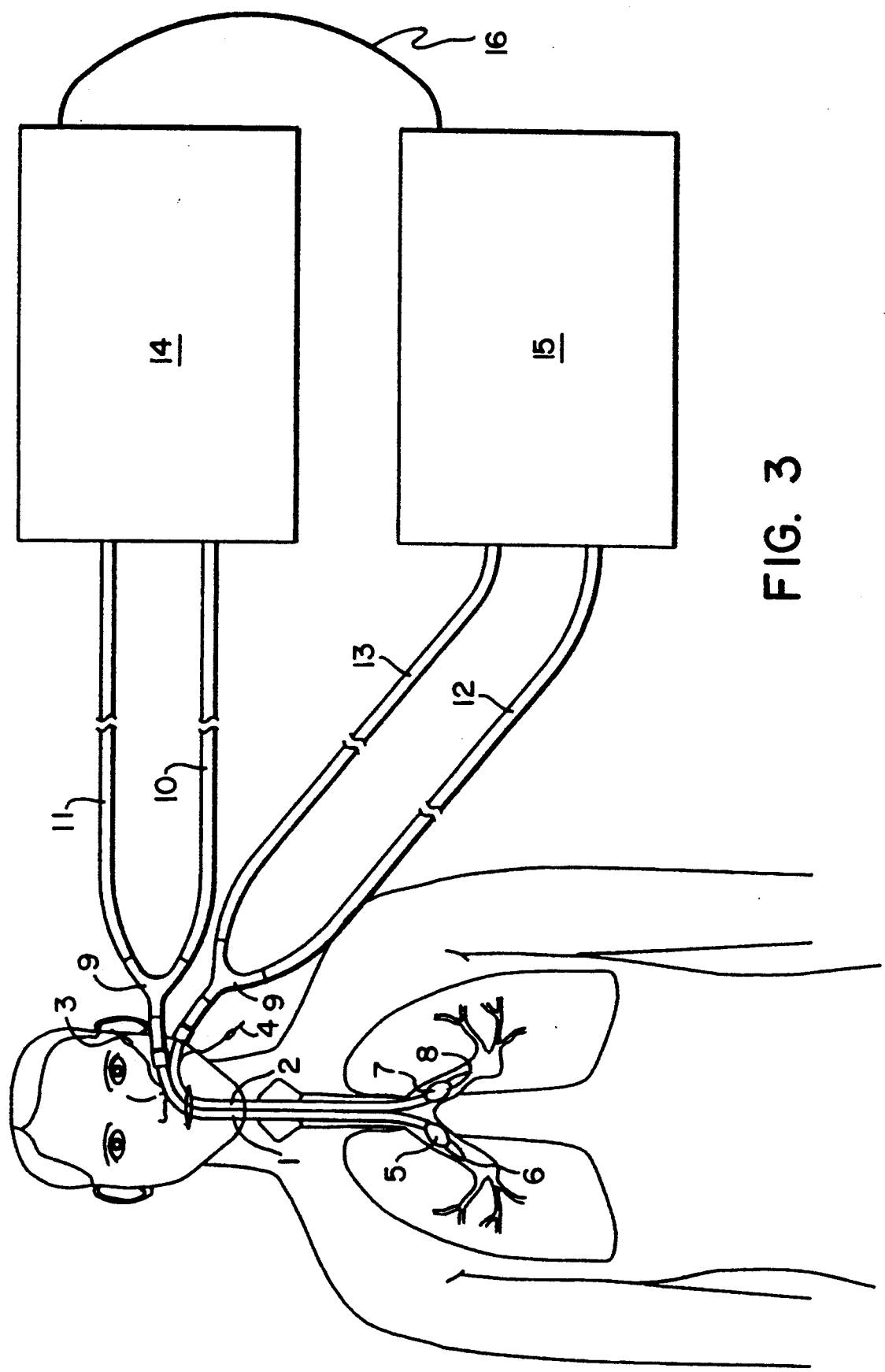
FIG. 3 is a schematic illustration of the prior art in which two ventilators are being used on a patient to provide for independent lung ventilation with the ventilators cycling simultaneously.

FIG. 3 illustrates a conventional prior art method of independent lung ventilation using a double lumen endotracheal tube with a pair of ventilators being operably connected by a sychronization cable. Independent lung ventilation allows each lung to be ventilated independently of the other using different ventilator parameters on each machine (as noted above), with the exception of the rate setting. This illustration is identical to FIG. 2, except that a standard connecting cable 16 synchronizes the ventilators so that they both cycle off and on simultaneously. An example of such arrangement would be the use of two Servo 900 C/D ventilators with a synchronization cable commercially available from Siemens-Elema, Part No. 90 27 046 E347E.

Figure 4:
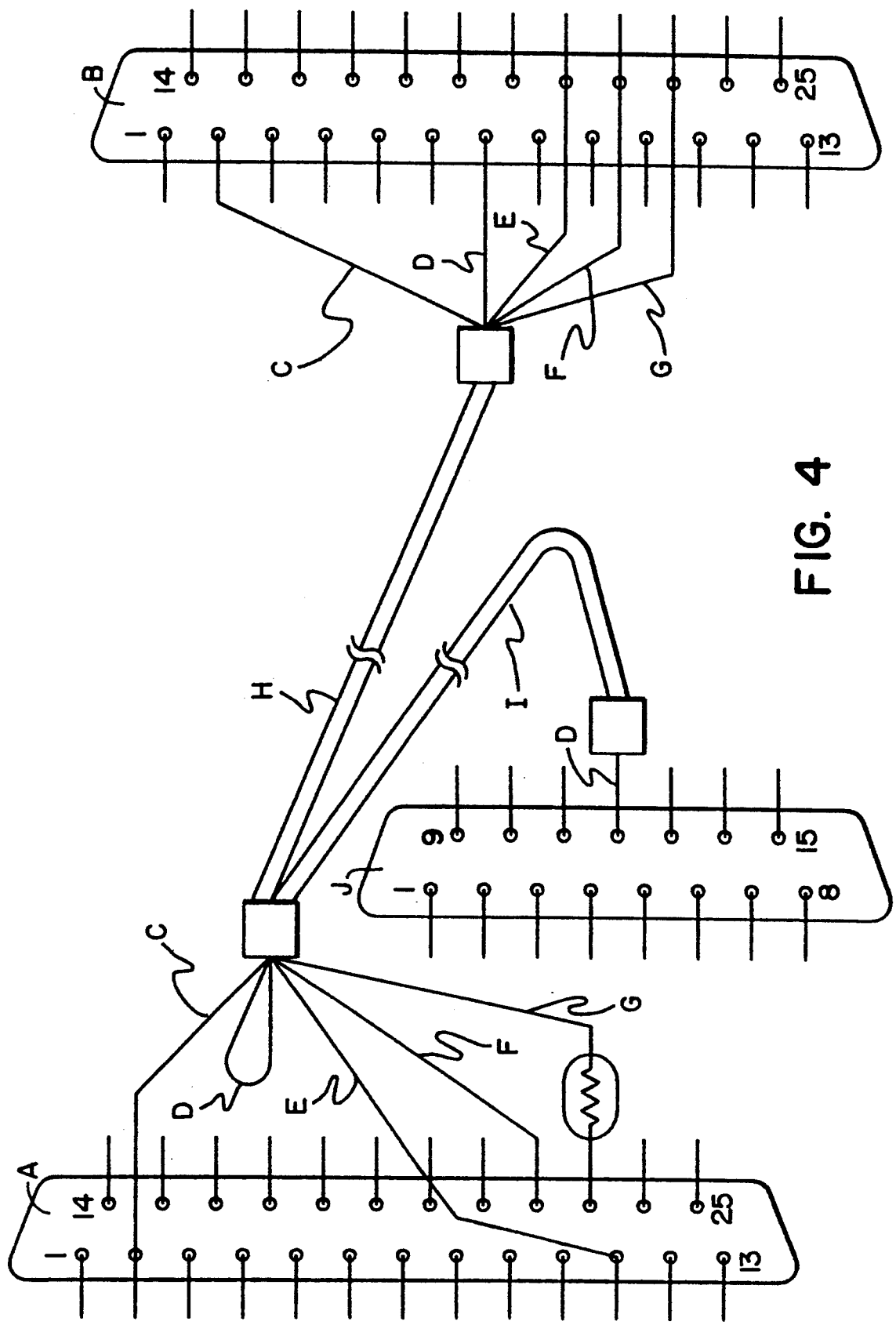
FIG. 4 is a schematic illustration of the electronic connection cable for asynchronous cycling of two Siemens 900 C or D ventilators according to the present invention.

FIG. 4 is a schematic of the invention, as embodied in the electrical connection cable for asynchronous cycling of two Siemens Servo 900 C/D ventilators. The two 25-pin connectors A and B are respectively labeled "Master" and "Slave" and plug into the 25-pin connector ports labeled "Control Terminal" at the rear of each ventilator. The present invention utilizes a 15-pin connector J to plug into the "Auxiliary Input" on the back of the Master Servo 900 C/D. When needed, it provides a connection via wire D of the auxiliary input pin #12 to pin #7 of the 25-pin connector on the rear of the Slave ventilator. Wire D merely passes through the Master connector A's housing and has no electrical contact with any of the 25-pins. Its function is to reset the alternating of the start of the inspiratory phase in the two machines. Depending on the phase the first machine is in when the second is turned on, or when the cable is connected to two running machines, the ventilators could potentially be in synchronism or the Slave ventilator could be holding the inspiratory phase indefinitely and not cycling over to the exhalation phase. To reset the ventilators to cycle asynchronously, or to terminate the inspiratory phase holding, the 25-pin connectors will be allowed to remain plugged into their respective machines, but the 15-pin auxiliary input connector will be unplugged from the Master machine. At this point, the auxiliary input may be re-connected briefly, then removed again and now left disconnected. Or, instead of connecting the auxiliary input connector at all, briefly switching the mode selector knob of the Master ventilator to another mode will restart asynchronous cycling (e.g. changing from Pressure Control mode to Volume Control mode for one breath, then returning to Pressure Control mode).

The clinical practitioner has the ability to adjust the time durations of the different phases, thus adjusting mean pressures, by manipulating flow rates or percent of inspiratory time ($\%T_I$) of the two machines. Therefore, by using various combinations of flow rates, or $\%T_I$: 1) the gap between the cycling of the two machines can be lengthened or shortened, 2) the gap can be omitted, or 3) the inspiratory phases can be overlapped when the inspiratory time is at a long enough setting in one or both machines.

The two wires C are joined together and connect pin #2 in each of the 25-pin connectors. They serve as electrical reference #21 in the Slave ventilator connector. This wire serves as the timing device for both ventilators and disengages the Slave's clock. Wire F connects pin #22 in each 25-pin connector, and serves to coordinate the cycling of the ventilators in response to the patient's triggering of the sensitivity setting. Wire G connects pin #23 in each connector and contains a 10K (+10) ohms resistor at the Master end. This wire serves to terminate the inspiration of either ventilator when the upper pressure limit setting is reached. The aforementioned wires are contained in housing to make up one joining cable H and the auxiliary input cable branch I.

Figure 5:
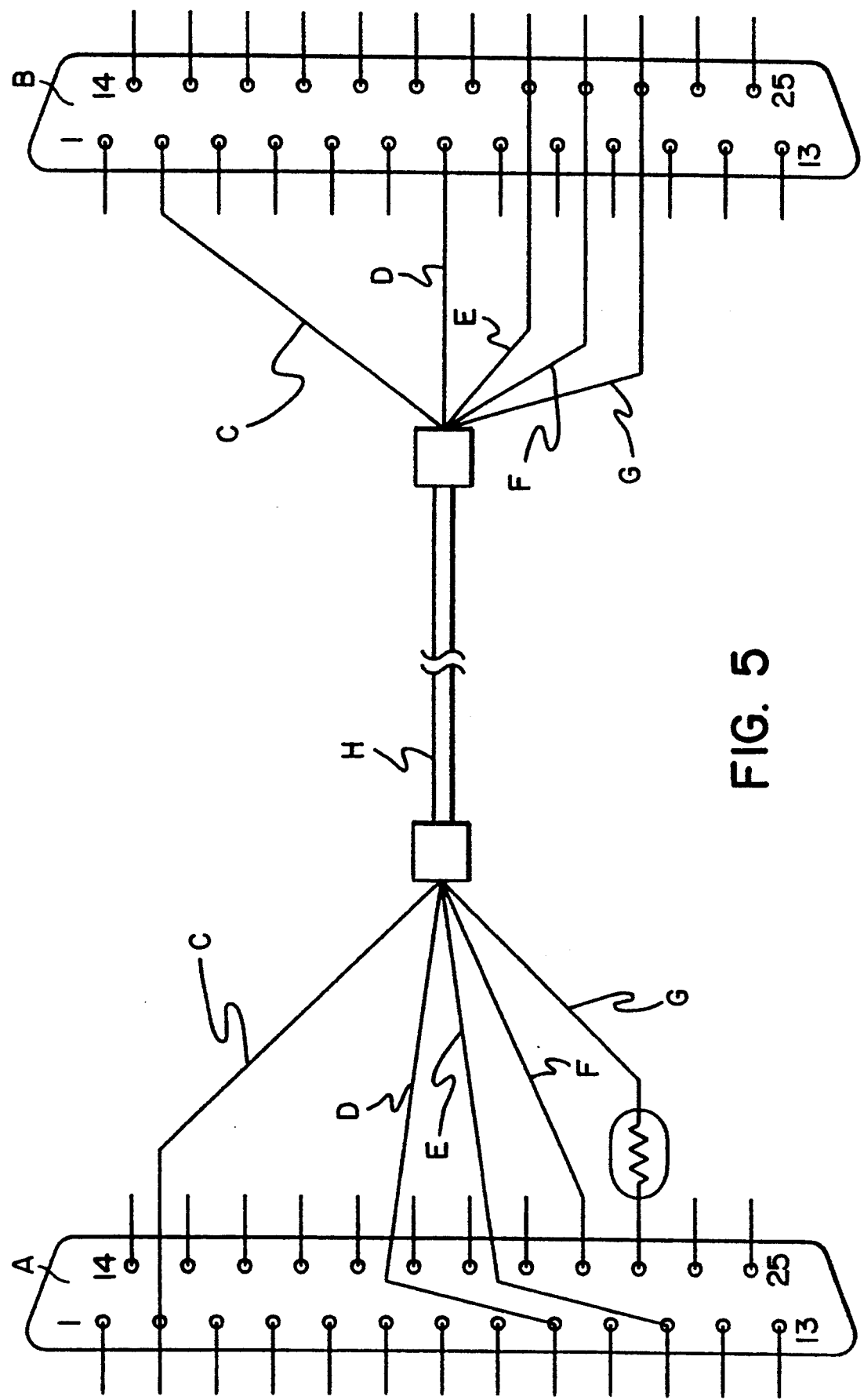
FIG. 5 is a schematic illustration of a commercially available connection cable which serves to control two Siemens 900 C or D ventilators to cycle in synchronization.

FIG. 5 is the schematic of the commercially available synchronization connection cable from Siemens Life Support Systems, Part No. 90 27 046 E347E. FIG. 5 is similar to FIG. 4, except that wire D connects pin #9 in the Master ventilator to pin #7 in the Slave ventilator. This serves to start inspiration in both machines simultaneously. Thus, the 15-pin auxiliary input connector of the Master is not used.

Figure 6:
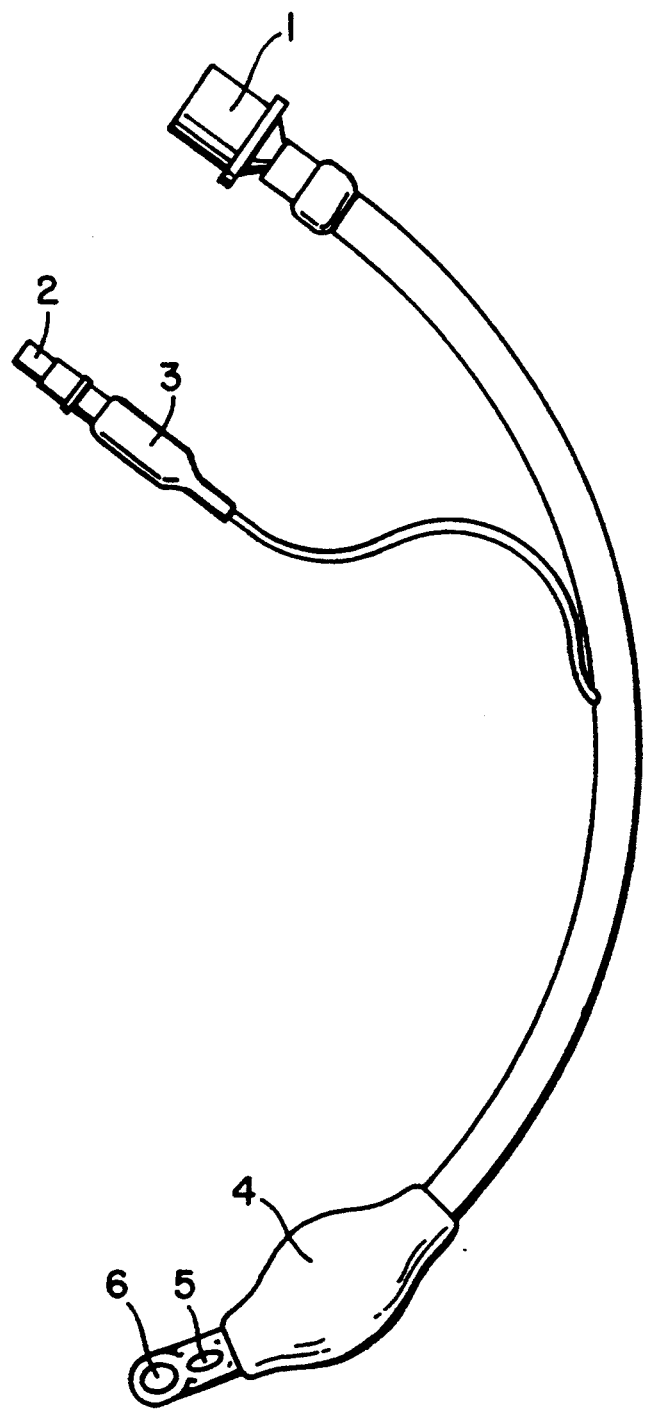
FIG. 6 illustrates a commercially available endotracheal tube.

FIG. 6 illustrates a commercially available standard endotracheal tube as shown in use in FIG. 1. The 15 mm O.D. connector 1 connects to a standard ventilator circuit (not shown). The pilot balloon injector port 2 provides for inflation and deflation of the cuff 4, which maintains an air seal against the tracheal wall. The pilot balloon's pressure indicating chamber 3 provides access to monitor the pressure contained in the cuff 4 without exact measurement with a cuff manometer. Ports #5 and 6 are openings at the distal end of the endotracheal tube which allow for gas exchange between the lungs and the tube (thus, the ventilator and lungs).

Figure 7:
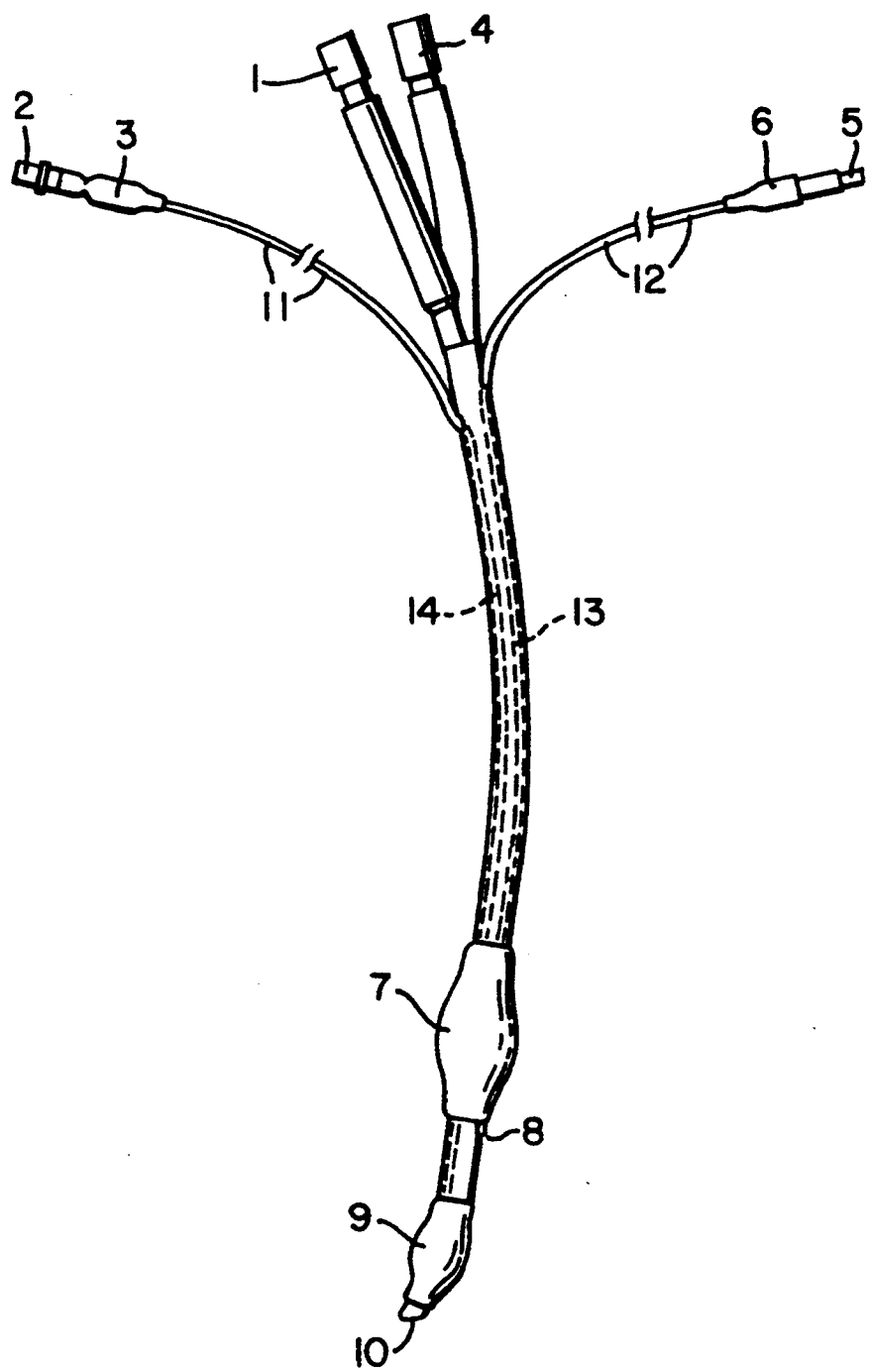
FIG. 7 illustrates a commercially available double-lumen endotracheal tube.

FIG. 7 illustrates an example of a commercially available double-lumen endotracheal tube as shown in use in FIG. 2 and 3. The 15 mm O.D. connectors 1 and 4 connect the circuit from each ventilator to the right 14 and the left 13 lumens, respectively. The pilot balloons 2 and 5, pressure-indicating chambers 3 and 6, and air conducting lines 11 and 12 provide for inflation and deflation of the right mainstem cuff 9 and the tracheal cuff 7, respectively. The right lumen's cuff 9 isolates the right lung by maintaining a seal at the level of the right mainstem bronchus and provides a closed circuit for gas exchange through the port 10. The port of the left lumen 8 allows for gas exchange of the left lung, which is isolated between the tracheal cuff 7 and the right mainstem bronchus cuff 9.

Double-lumen endotracheal tubes come in several minor variations to this, such as with a left mainstem and a tracheal cuff. Therefore, instead of the left lung being isolated between the tracheal cuff and the right mainstem cuff as shown, the right lung can be isolated in a similar fashion.

In operation of the embodiment illustrated in FIG. 1, two ventilators are electronically linked by the cable #15/16 to provide asynchronous cycling of the ventilators which are connected to an endotracheal tube and a pneumobelt, respectively. The objective is to alternate the triggering of two ventilators so that they do not cycle on and off at the same time. One ventilator is connected to the patient's endotracheal tube to ventilate the patient, while the other intermittently inflates an air bladder tightly wrapped around the upper abdominal area. This air-bladder assembly, as previously discussed, is sometimes referred to as a pneumobelt. This device intermittently applies external pressure to the liver to cause an increased blood flow from the liver to the heart and thoracic vessels. This helps to attain several objectives. First, the cardiopulmonary circulation is improved because the increased blood flow from the liver plays a significant role in overcoming the pulmonary vascular resistance. Thus, oxygenation is increased with the increased perfusion. Secondly, the patient's hypotensive state is expected to be less severe. And finally, the patient experiences a shorter duration of life-threatening hypoxemia and hypotension. This application is most common in cardiac procedures such as, but not limited to, the Fontan Procedure.

In the system of the present invention, a synchronization cable part #90 27 046 E347E, made by Siemens Life Support Systems, is used (FIG. 5). This cable was designed originally to synchronize two ventilators for independent lung ventilation. In this invention, however, the cable has been modified (FIG. 4) as follows to perform the exact opposite function that it is intended to perform.

The modification to the pre-existing cable is done at the end labeled "Master Ventilator", and consists of the following steps:
   A. The brown wire connected to pin 9 was desoldered and removed.
   B. This wire is soldered to an extending wire which is connected to pin 12 of a 15-pin connector.
   C. This 15-pin connector can be plugged into the Auxiliary input on the "Master Ventilator".

The "Master Ventilator" end is plugged into the control terminal of the ventilator which will be used to ventilate the patient, while the opposite end, labeled "Slave Ventilator" plugs into the control terminal of the ventilator to be connected to the pneumobelt or other device. Although the ventilators can be reversed, connecting the Slave to the pneumobelt or other similar device allows for the interruption of the functioning of said device, without interrupting the ventilation of the patient.

As previously noted, the present invention as shown in FIG. 4 is currently embodied in a pair of Siemens Servo 900 C/D Ventilators. The rear of each machine contains a set of conventional 15-pin, 25-pin and 37-pin, "Cannon" connectors, providing for connection of auxiliary equipment, control terminal and recorder output (not shown), respectively.

Figure 8B:
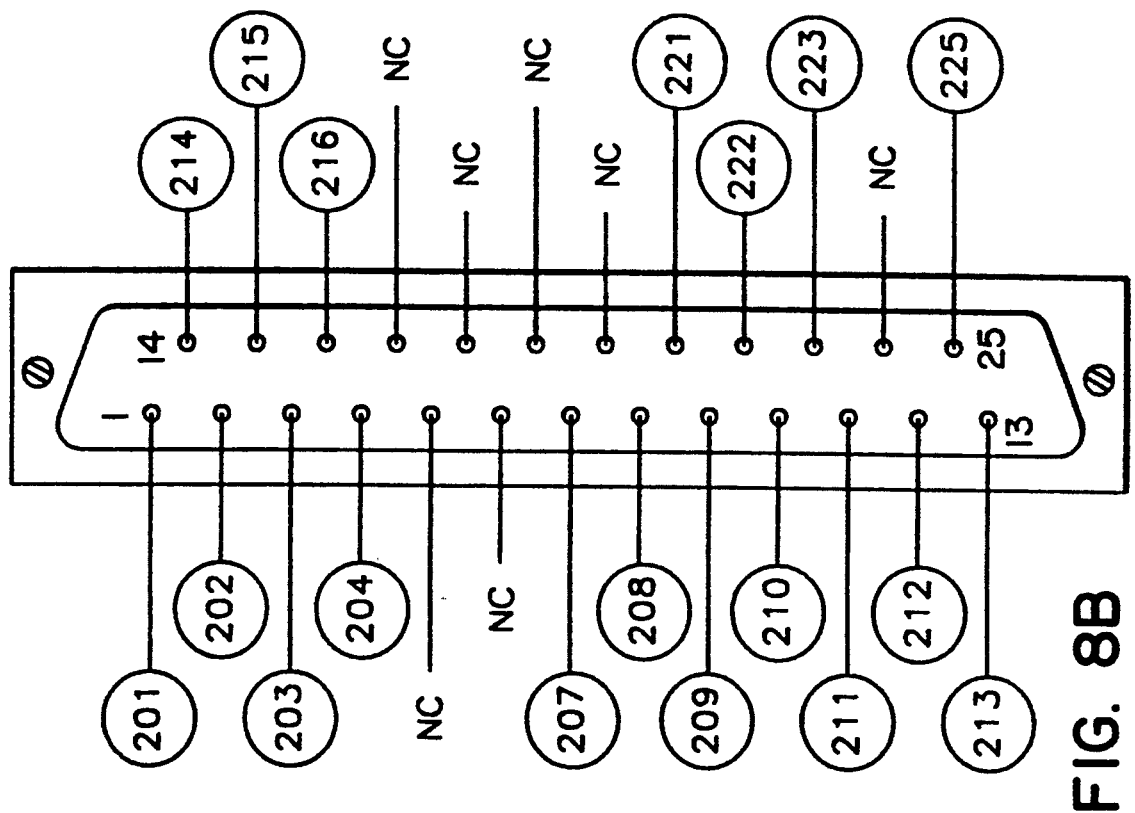
FIG. 8 illustrates the cable pin connections suitable for use with ventilators of the present invention.
Figure 8A:
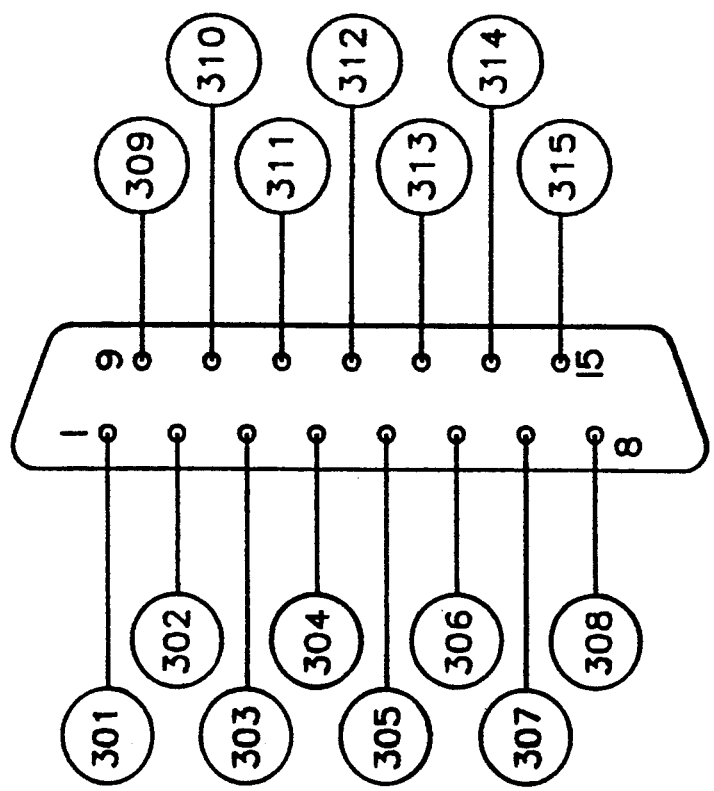

FIG. 8 shows such of these sets as is necessary to explain using the Siemens machines in the practice of the present invention, in particular, the 25-pin connector which is the Master connector of either FIG. 4 or FIG. 5, and FIG. 4's 15-pin auxiliary input connector, which is one of three such connectors on the Siemens machine.

In FIG. 8, the reference numerals 301-315 correspond, in order, to the standard numbering 1-15, of pins/sockets on a 15-pin "Cannon" connector. Reference numerals 201-225 likewise correspond, in order, to the standard numbering 1-25, of pins/sockets on a 25-pin "Cannon" connector. Moreover, each of the connections to the Master machine's internal circuitry (not shown) is labeled with the appropriate use, function or parameter corresponding to places in said circuitry to which the connectors provide electrical connection. The Slave machine's connectors, FIGS. 4 and 5, and internal circuitry (not shown) to which the Slave connector provides connection, are identical to those of the Master machine, so therefore are not shown in FIG. 8, as it would be redundant to duplicate in FIG. 8 the labeling and the connector. The auxiliary connectors in the Slave machine are not used in either synchronization or asynchronization.

As will be seen from FIG. 5, in the prior art cable, the wire D would normally connect (in terms of FIG. 8) a pin 209, labeled MASTER START INSPIRATION, to pin 207 labeled SLAVE START INSPIRATION, the former pin being on the Master connector, and the latter being on the Slave connector (not shown in FIG. 8). However, according to FIG. 4, which illustrates the invention, but, again in terms of FIG. 8, the wire D bypasses the Master connector pin 209 and goes into the auxiliary input connector and connects to pin 312 where, as FIG. 8 shows, it is labeled EXPIRATION TIME OUT.

It will be observed that there are more pins than are interconnected by the cabling between the machines. There are also more labeled pins on the illustrated connectors than there are wires in the cables shown in FIGS. 4 and 5. This is because in the first place, "Cannon" connectors in their various uses often have more pins than will be used (in this case, those marked NC in FIG. 8). Secondly, some of the pins provide alternate electrical parameters (e.g., pins 1–4 of the Master connector). Finally, the machines are capable of a variety of prior art uses or functions, singly or together, or with other kinds of equipment.

In other words, only those pin connections, as follows, are involved in the asynchronous cycling configuration of the present combination of pneumobelt and particular ventilators:

1. Wire C interconnects Master and Slave connectors' pins 202, OV REFERENCE.
2. Wire E interconnects Master connector's pin 211, MASTER CLOCK output, and Slave connector's pin 221, SLAVE CLOCK input.
3. Wire F interconnects Master and Slave connectors' pins 222, PATIENT TRIGGER.
4. Wire G interconnects Master and Slave connectors' pins 223, UPPER PRESSURE EXCEEDED.

Wire D allows for interconnection when needed, of the Master's auxiliary connector's pin 312, EXPIRATION TIME OUT, and Slave connector's pin 207, SLAVE START INSPIRATION. However, it plays no part in the asynchronous cycling configuration, once asynchronous cycling is underway.

However, please note that Wire D being disconnected from pin 209 of the Master machine uniquely characterizes the present invention. The occasional brief connection of wire D to the pin 312 of the Master auxiliary connection, while also unique, is not critical to the present invention, since, as pointed out elsewhere, asynchronism, etc., can be initiated otherwise than by connecting wire D to pin 312. The remainder of the interconnections, namely, those described in items 1, 2, 3 and 4 supra, are standard features: a reference voltage, such as in item 1; timing control, as in item 2; options as in item 3, patient trigger; and safety features, as in item 4, pressure limit; and hence are not limitations critical to the operating principle of the present invention.

The application of the technique of asynchronous cycling of two mechanical ventilators, or the future addition of a mode that serves the same purpose on a single machine, has multi-faceted application. The use of said technique includes 1), Alternating Lung Ventilation, whereby each lung could be ventilated independently of the other, but in alternating fashion, via a commercially available double lumen endotracheal tube (FIG. 7), and 2), ventilating the patient with conventional mechanical ventilation using one ventilator connected to a standard endotracheal (or tracheostomy) tube while the second ventilator can be utilized to alternately pressurize or inflate a biomedical device, such as an externally applied pneumobelt (FIG. 1).

This invention overcomes the significant flaw which has been present when two ventilators are used simultaneously: previously there was no method of coordinating the cycling of the two ventilators, except in the case of Servo 900 C ventilators which could be linked to function only concurrently. Therefore, the two ventilators could simultaneously cycle on and reach maximum pressure levels at the same time. Thus, the functional effects of the pneumobelt on the liver are negated because the peak inspiratory pressure experienced by the lungs prevent the thoracic blood return to occur at its maximum efficiency. Alternating these two pressure peaks provides the optimal result from both ventilators.

The early research surrounding this invention was initiated based on the need to coordinate the utilization of two ventilators simultaneously. This need is perhaps most evident specifically in surgical patients who undergo the Fontan Procedure, when one machine is used to ventilate the patient via a standard endotracheal tube while a second ventilator is used to pressurize a pneumobelt or similar device applied externally around a patient. Young patients who undergo the Fontan Procedure experience successful physiologic correction in the operating room, only to face post-operative, life-threatening hypoxemia and hypotension.

The present invention, as previously stated, is based on its application to alternately ventilate a patient and pressurize a pneumo belt or any similar device that provides external localized pressure for a specific purpose. In the case of the Fontan procedure, whereby the patient is left with a non-functional right ventricle, the external pressure is intermittently applied to the abdominal area to increase return from the hepatic and splenic blood supply to the thoracic cardiovascular system. The resultant effect is analogous to an "external blood pump" which utilizes primarily the hepatic system's blood volume to increase preload and to help overcome the pulmonary vascular resistance. Thus, by increasing cardiac preload the hypotension is diminished, pulmonary perfusion increased, and as a result, arterial blood oxygenation increases. The two major factors in surviving the initial post-operative stage of the Fontan procedure, severe hypoxemia and hypotension due to low cardiac output, are aided by this mechanical mechanism along with the normal medical treatment (i.e. pharmacological agents) for hypotension. The ultimate goal of this invention is to significantly decrease the mortality rate by alternating the lung ventilation with the pneumo belt in the critical hours immediately following surgery.

The Fontan procedure is one process within the scope of cardiac surgery by which a physiologic correction or repair of tricuspid atresia is accomplished. The Fontan procedure is used for many cardiac anomalies which involve only one functional ventricle, although its most common application might be in cases of tricuspid atresia. In tricuspid atresia, any one of several anomalies can be present which result in improper or absent blood flow directly between the right atrium and right ventricle. Tricuspid atresia is the third most common congenital heart realformation which causes cyanosis, after tetralogy of Fallot and transposition of the great arteries. (Robert M. Sode and Derek A. Fyfe, "Tricuspid Atresia," in *Surgery of the Chest*, 5th ed., Vol. II, ed. David C. Sabaston, Jr., M.D., and Frank C. Spencer, M.D. (Philadelphia: W. B. Saunders Company, 1990), p. 1461.)

Font an patients suffer a relatively high mortality rate of approximately 40%, depending on pre-operative risk factors involved and the strictness of the adherence to candidate selection criteria. Although 40% mortality rate is not uncommon, it may be possible to decrease mortality to below 20% when Fontan candidates are very selectively screened. Conversely, mortality rate increases when a patient presents with multiple risk factors. Selection criteria for the Fontan procedure (ibid., p. 1472) include 1) age—usual range of 3-16 years, but preferably before 6 years, 2) normal sinus rhythm, 3) normal drainage of the vanae cavae, 4) normal volume of the right atrium, 5) mean pulmonary artery pressure less than or equal to 15 mm Hg., 6) pulmonary vascular resistance index less than 4 units/m$^2$; if less than 2 units/m$^2$ operative survival is considered good, if it is 2-4 units/m$^2$ survial is considered satisfactory, 7) pulmonary artery - aortic diameter ratio greater than or equal to 0.75, 8) normal function of the dominant ventricle, determined by an ejection fraction of at least 0.6, 9) no mitral incompetence, and 10) no impairing effects of a previous shunt.

The normal cardiopulmonary circulation includes systemic blood return to the right atrium, through the tricuspid valve to the right ventricle, through the pulmonic valve and is carried through the pulmonary artery to the pulmonary capillary membrane bed. Therefore, the right ventricle provides the means to perfuse the pulmonary vasculature so that gaseous exchange can occur. The blood flow then returns to the heart through the pulmonary vein to the left atrium and through the mitral, or bicuspid valve into the left ventricle. It is then pumped out the aortic valve to the aorta, and finally throughout systemic circulation.

The post-operative Font an patient deviates significantly from the normal contiguous circulatory route. Although modifications to the Fontan procedure may be done based on the individual patient, the surgical procedure results in systemic venous blood being returned directly to the pulmonary artery, totally bypassing the right atrium, tricuspid valve, right ventricle and pulmonic valve. Therefore, the right ventricle contributes nothing to the injection of blood into the pulmonary vasculature. Although there is very little to push the systemic venous blood, once it is in the pulmonary artery it circulates into the pulmonary vasculature. As in the normal heart, it then returns through the pulmonary vein to the left atrium and through the mitral, or biscuspid valve into the left ventricle and is then pumped throughout systemic circulation. The left ventricle is the sole means of circulating blood into both the sytemic and the pulmonary systems.

Immediately following surgery the hemodynamic system of the patient must undergo significant adjustment to the surgical alterations that were performed. It is in this initial adjustment period of the first 24-48 hours when the enablement of this invention may have greatest application. When the two ventilators are operated in alternating fashion to ventilate the patient and to pressurize the pneumobelt, the two resulting peak pressures are not allowed to occur simultaneously. Occurring simultaneously would cause the intrathoracic pressure from the ventilation of the lungs to diminish or negate the effects of the pneumobelt. Conversely, when these pressure peaks are alternated, the pneumobelt can more efficiently and effectively aid in the pulmonary perfusion transcending the pulmonary vascular resistance, resulting in a decrease in the hypoxic and hypotensive conditions. The intention of the application of this invention is to significantly reduce the mortality rate of 40% in these children.

While the invention has been described in detail with respect to specific embodiments thereof, it will be understood by those skilled in the art that variations and modifications may be made without departing from the essential features thereof.

What is claimed is:

1. A ventilator system comprising:
    an inflatable bladder worn by a subject;
    a first ventilator connected to said inflatable bladder, said first ventilator having an input signal receiver;
    an endotracheal tube inserted into said subject;
    a second ventilator having an input signal receiver and being connected to said endotracheal tube;
    means for generating signals representative of the start of each of patient inspiration and expiration;
    means for transmitting said signal representative of patient expiration start time from said first ventilator to said input signal receiver of said second ventilator;
    means for starting patient expiration on said first ventilator; and
    means for starting patient inspiration on said second ventilator responsive to the receipt of said signal representative of said expiration start time and following patient expiration, said first and second ventilators thereby operating asynchronously.

2. The ventilator system of claim 1 wherein said first ventilator comprises a master ventilator and said second ventilator comprises a slave ventilator.

3. The ventilator system of claim 2 wherein said master ventilator comprises a Siemens Servo Ventilator 900 C/D.

4. The ventilator system of claim 3 wherein said slave ventilator comprises a Siemens Servo Ventilator 900 C/D.

5. The ventilator system of claim 2 wherein said transmitting means comprises electrical connection of a start inspiration pin on said slave ventilator to an expiration time out pin on said master ventilator.

6. The ventilator system of claim 4 wherein said transmitting means comprises electrical connection of pin 7 on the control terminal of said slave ventilator to pin 12 on the auxiliary equipment of said master ventilator.

7. The ventilator system of claim 1 wherein said first ventilator and said second ventilator are contained in a single outer housing.

8. The ventilator system of claim 1 wherein said transmitting means comprises a cable.

9. A method for connecting a first ventilator to a second ventilator for asynchronous cycling which method comprises:
    providing an inflatable bladder worn by a subject;
    providing a first ventilator having an input signal receiver;
    connecting said first ventilator to said inflatable bladder;

providing an endotracheal tube inserted into said subject;

providing a second ventilator having an input signal receiver;

connecting said second ventilator to said endotracheal tube;

generating signals representative of the start of each of patient inspiration and patient expiration;

transmitting said signal representative of patient expiration start time from said first ventilator to said input signal receiver of said second ventilator;

starting patient expiration on said first ventilator; and starting patient inspiration on said second ventilator responsive to the receipt of said signal representative of said expiration start time and following patient expiration, said first and second ventilators thereby operating asynchronously.

10. The method of claim 9 wherein said transmitting comprises electrical transmission through a cable means.

11. A ventilator system comprising:

a double lumen endotracheal tube inserted into a subject;

a first ventilator connected to one lung of said subject by one lumen of said double lumen endotracheal tube, said first ventilator having an input signal receiver;

a second ventilator having an input signal receiver and being connected to the other lung of said subject by the other lumen of said double lumen endotracheal tube;

means for generating signals representative of the start of each patient inspiration and patient expiration;

means for transmitting said signal representative of patient expiration start time from said first ventilator to said input signal receiver of said second ventilator;

means for starting patient expiration on said first ventilator; and means for starting patient inspiration on said second ventilator responsive to the receipt of said signal representative of said expiration start time, said first and second ventilators thereby operating asynchronously.

12. A method for connecting a first ventilator to a second ventilator for asynchronous cycling which method comprises:

providing a double lumen endotracheal tube inserted into a subject;

providing a first ventilator having an input signal receiver;

connecting said first ventilator to one lung of said subject by one lumen of said double lumen endotracheal tube;

providing a second ventilator having an input signal receiver;

connecting said second ventilator to the other lung of said subject by the other lumen of said double lumen endotracheal tube;

generating signals representative of the start of each of patient inspiration and patient expiration;

transmitting said signal representative of patient expiration start time from said first ventilator to said input signal receiver of said second ventilator;

starting patient expiration on said first ventilator; and starting patient inspiration on said second ventilator responsive to the receipt of said signal representative of said expiration start time, said first and second ventilators thereby operating asynchronously.

* * * * *